Sept. 23, 1958 F. W. ANDERSON Plant Pat. 1,754

PEACH TREE

Filed Feb. 3, 1958

WITNESS

Addison E. Avery

INVENTOR.

Frederic W. Anderson

Webster & Webster

ATTYS.

United States Patent Office

Plant Pat. 1,754
Patented Sept. 23, 1958

1,754

PEACH TREE

Frederic W. Anderson, Merced, Calif., assignor to Kim Bros., a copartnership doing business under the fictitious name and style of Reedley Nursery, Reedley, Calif.

Application February 3, 1958, Serial No. 713,072

1 Claim. (Cl. 47—62)

The present invention relates to a new and distinct variety of peach tree which bears large, yellow fleshed, freestone fruit, essentially characterized by a ripening period in September; the harvest being a few days after the Kirkman Gem peach (United States Plant Patent No. 506) and shortly before the Merrill Fiesta peach (United States Plant Patent No. 1,099).

The instant variety of peach tree was originated by me, in my experimental orchard located near Merced, California, as a result of an extensive and continuing plant breeding program, one of the objects of which was to obtain improved peach and nectarine varieties having commercially acceptable fruit ripening in the month of September.

More particularly, the variety was originated by me as follows:

A Le Grand nectarine (United States Plant Patent No. 549) was crossed with a number of September ripening peaches and all of the seedling progeny were peaches; one of which was observed to have various superior qualities for further breeding.

I therefore back-crossed such one peach with the Le Grand nectarine, and of the seedling progeny from such back-crossing approximately one-half were nectarines and the other one-half peaches.

When these latter seedlings reached maturity the present variety was selected therefrom as being especially promising, as it bore fruit of the yellow fleshed, freestone class having excellent eating and shipping qualities, and additionally ripened—desirably—between the Kirkman Gem peach and the Merrill Fiesta peach, and approximately two to three weeks later than the Rio Oso Gem peach (United States Plant Patent No. 84).

As compared to said Kirkman Gem and Merrill Fiesta peaches the present variety is characterized by a more vigorous and productive tree, and fruit which is larger, firmer of flesh, more exterior red color, longer keeping quality with less rapid deterioration, less acid in flavor, a smoother and less conspicuous suture line, and a less prominent apical point.

Subsequent to its origination the variety was asexually reproduced by me as top-workings on mature trees in my experimental orchard, located as aforesaid, and such reproductions were found to run true in all respects.

Figure 1:
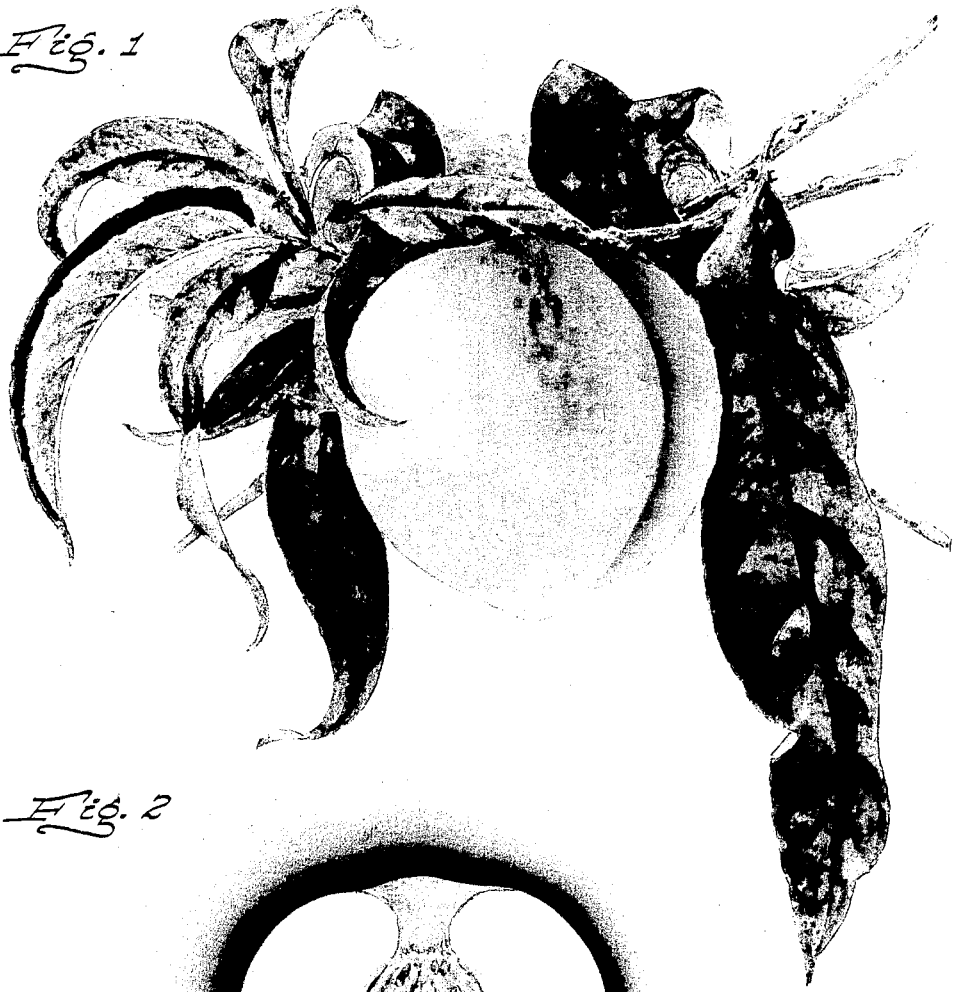
Fig. 1 is a sectional elevation showing one of the peaches, together with twigs and leaves.
Figure 2:
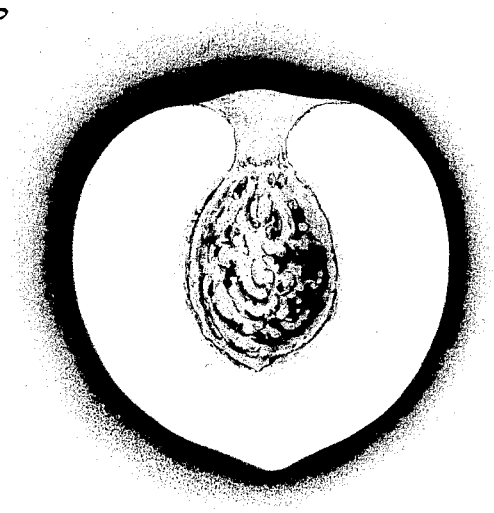
Fig. 2 is a sectional elevation of one of the peaches, with the stone exposed.

Referring now more specifically to the pomological details of this new and distinct variety of peach tree, the following is an outline description thereof; all major color plate identifications being by reference to Maerz and Paul Dictionary of Color:

Tree:
- *Size.*—Large.

- *Vigor.*—Vigorous.
- *Growth.*—Spreading.
- *Production.*—Productive.

Trunk:
- *Size.*—Stocky to medium.

Branches:
- *Size.*—Stocky to medium.

Leaves:
- *Size.*—Large to medium. Average length—6¼". Average width—1¼".
- *Margin.*—Crenate.
- *Petiole.*—Medium length.
- *Glands.*—Average number—three to five. Alternate; medium size; reniform. Usually positioned two on petiole and two to three on blade.
- *Stipules.*—None.
- *Color.*—Top side—medium green (22–L–8). Under side—lighter green (22–H–6).

*Flower buds:*
- Medium size, medium length.

Flowers:
- *Blooming period.*—Midseason.
- *Size.*—Large.

Fruit:
- *Maturity when described.*—Eating ripe—September 15, 1957.
- *Date of first picking.*—September 7, 1957.
- *Date of last picking.*—September 17, 1957.
- *Size.*—Large. Average diameter axially—3¼". Average transversely in suture plane—3½".
- *Form.*—Uniform; symmetrical; globose to somewhat oblate.
- *Suture.*—Distinct; shallow; extends from base to beyond apex; marked depression beyond pistil point.
- *Ventral surface.*—Rounded.
- *Cavity.*—Elongated in suture plane with suture showing on ventral side.
- *Base.*—Oblique.
- *Apex.*—Short; depressed.
- *Pistil point.*—Apical.

Skin:
- *Thickness.*—Medium.
- *Texture.*—Medium.
- *Tendency to crack.*—None.
- *Down.*—Moderate; medium length.
- *Color.*—Yellow (10–J–6 to 11–D–11), overspread to a substantial extent with red (4–L–9 to 7–L–7); the red being distinctly mottled.

Flesh:
- *Juice.*—Abundant.
- *Texture.*—Firm; meaty; melting.
- *Fibers.*—Fine; tender.
- *Ripens.*—Even.
- *Flavor.*—Subacid.
- *Aroma.*—Distinct.
- *Eating quality.*—Good to best.
- *Color.*—Yellow (9–L–4 to 9–L–6), with a reddish cast (3–J–9) near stone.

Stone:
- *Type.*—Free.
- *Size.*—Medium. Average length—1 5/16". Average breadth—1". Average thickness—¾".
- *Form.*—Obovoid.
- *Base.*—Straight.
- *Hilum.*—Broad; oblong.
- *Apex.*—Rounded.
- *Sides.*—Equal.
- *Surface.*—Irregularly furrowed near base; pitted throughout.
- *Ridges.*—Jagged; continuous.
- *Pits.*—Elongated.

*Ventral edge.*—Thick.

*Dorsal edge.*—Narrow, with deep broad groove throughout.

*Tendency to split.*—Slight.

*Color.*—Reddish brown (6–A–12 to 6–H–12).

Use: Market; local; dessert.

Keeping quality: Good.

Shipping quality: Good.

The tree and its fruit herein described may vary in slight detail due to climatic and soil conditions under which the variety may be grown.

The following is claimed:

A new and distinct variety of peach tree, as illustrated and described, which bears large fruit of the yellow fleshed, freestone class, particularly characterized by ripening after the Kirkman Gem peach, before the Merrill Fiesta peach, and approximately two to three weeks than the Rio Oso Gem peach; and further characterized—in comparison to said Kirkman Gem and Merrill Fiesta peaches—by a tree which is more vigorous and productive, and by fruit of larger size, firmer flesh, more exterior red color, longer keeping quality, a less acid flavor, a smoother and less conspicuous suture line, and a less prominent apical point.

No references cited.